(12) United States Patent
Bailey (10) Patent No.: US 9,439,411 B2
(45) Date of Patent: Sep. 13, 2016

(54) FISHING STATISTICS DISPLAY

(71) Applicant: Navico Holding AS, Egersund (NO)

(72) Inventor: Paul Robert Bailey, Ellerslie (NZ)

(73) Assignee: NAVICO HOLDING AS, Egersund (NO)

( * ) Notice: Subject to any disclaimer, the term of this patent is extended or adjusted under 35 U.S.C. 154(b) by 166 days.

(21) Appl. No.: 14/107,933

(22) Filed: Dec. 16, 2013

(65) Prior Publication Data

US 2015/0054828 A1 Feb. 26, 2015

Related U.S. Application Data

(60) Provisional application No. 61/868,444, filed on Aug. 21, 2013.

(51) Int. Cl.
*G06T 11/20* (2006.01)
*A01K 97/00* (2006.01)
(Continued)

(52) U.S. Cl.
CPC ............... *A01K 97/00* (2013.01); *A01K 79/00* (2013.01); *A01K 99/00* (2013.01); *A61B 5/1118* (2013.01); *A61B 5/1123* (2013.01); *G01B 21/00* (2013.01); *G01C 21/20* (2013.01); *G01C 21/203* (2013.01); *G06F 3/014* (2013.01); *G06F 3/017* (2013.01); *G06F 3/0231* (2013.01); *G06F 3/0346* (2013.01); *G06F 11/3438* (2013.01); *G06F 11/3476* (2013.01); *G06F 15/0225* (2013.01); *G06F 17/30867* (2013.01); *G06K 9/00342* (2013.01); *G06Q 10/00* (2013.01); *G06Q 50/01* (2013.01); *G06T 7/2033* (2013.01); *G06T 7/2093* (2013.01); *G06T 7/60* (2013.01); *G06T 11/206* (2013.01); *G08C 17/02* (2013.01); *G11B 27/031* (2013.01); *G11B 27/17* (2013.01); *G11B 27/28* (2013.01); *G11B 27/34* (2013.01); *G11B 31/006* (2013.01); *H04Q 9/00* (2013.01); *B63B 49/00* (2013.01); *G01S 7/003* (2013.01); *G01S 15/96* (2013.01); *G06F 11/3013* (2013.01); *G06F 11/3058* (2013.01); *G06F 2201/835* (2013.01); *G06T 2207/10016* (2013.01);
(Continued)

(58) Field of Classification Search
None
See application file for complete search history.

(56) References Cited

U.S. PATENT DOCUMENTS 4,829,493 A 5/1989 Bailey
4,879,697 A 11/1989 Lowrance et al.
(Continued)

FOREIGN PATENT DOCUMENTS

DE 102004059619 A1 6/2006
EP 1 561 377 A1 8/2005
(Continued)

OTHER PUBLICATIONS

SAS, "SAS BI Dashboard 4.31 User's Guide", Second Edition, by SAS Electronic book, Aug. 1, 2012, downloaded @http://support.sas.com/documentation/cdl/en/bidbrdug/65580/PDF/default/bidbrdug.pdf.*

(Continued)

*Primary Examiner* — Yingchun He
(74) *Attorney, Agent, or Firm* — Nelson Mullins Riley & Scarborough LLP (57) ABSTRACT

Various implementations described herein are directed to a method for displaying fishing statistics. The method may include displaying a path traveled by a fisherman or marine vessel. The path may be recorded using a positioning system. The method may include displaying fishing statistics along the path.

17 Claims, 5 Drawing Sheets

(51) Int. Cl.

| | | |
|---|---|---|
| *G08C 17/02* | (2006.01) | |
| *G06F 3/01* | (2006.01) | |
| *G06F 3/023* | (2006.01) | |
| *G06F 15/02* | (2006.01) | |
| *G06T 7/20* | (2006.01) | |
| *G06T 7/60* | (2006.01) | |
| *G11B 27/031* | (2006.01) | |
| *G11B 27/17* | (2006.01) | |
| *G11B 31/00* | (2006.01) | |
| *A01K 99/00* | (2006.01) | |
| *G01C 21/20* | (2006.01) | |
| *A61B 5/11* | (2006.01) | |
| *G01B 21/00* | (2006.01) | |
| *G06Q 10/00* | (2012.01) | |
| *G06Q 50/00* | (2012.01) | |
| *G06F 17/30* | (2006.01) | |
| *A01K 79/00* | (2006.01) | |
| *G06F 11/34* | (2006.01) | |
| *G06K 9/00* | (2006.01) | |
| *G11B 27/28* | (2006.01) | |
| *G11B 27/34* | (2006.01) | |
| *G06F 3/0346* | (2013.01) | |
| *H04Q 9/00* | (2006.01) | |
| *B63B 49/00* | (2006.01) | |
| *G01S 15/96* | (2006.01) | |
| *G06F 11/30* | (2006.01) | |
| *G01S 7/00* | (2006.01) | |

(52) U.S. Cl.
CPC . *G06T2207/30196* (2013.01); *G08C 2201/32* (2013.01); *H04Q 2209/43* (2013.01); *Y02B 60/165* (2013.01)

(56) References Cited

U.S. PATENT DOCUMENTS

| | | | |
|---|---|---|---|
| 5,025,423 A | 6/1991 | Earp | |
| 5,191,341 A | 3/1993 | Gouard et al. | |
| 5,321,391 A | 6/1994 | Fox | |
| 5,446,775 A | 8/1995 | Wright et al. | |
| 5,537,380 A | 7/1996 | Sprankle, Jr. et al. | |
| 5,546,695 A | 8/1996 | Langer | |
| 6,222,449 B1 | 4/2001 | Twining | |
| 6,225,984 B1 | 5/2001 | Crawford | |
| 6,252,544 B1 | 6/2001 | Hoffberg | |
| 6,263,147 B1 | 7/2001 | Tognazzini | |
| 6,321,158 B1 | 11/2001 | DeLorme et al. | |
| 6,411,283 B1 | 6/2002 | Murphy | |
| 6,418,080 B2 | 7/2002 | Inouchi | |
| 6,421,299 B1 | 7/2002 | Betts et al. | |
| 6,459,372 B1 | 10/2002 | Branham et al. | |
| 6,567,792 B1 | 5/2003 | Arnold | |
| 6,584,722 B1 | 7/2003 | Walls | |
| 6,587,740 B2 | 7/2003 | Byrne et al. | |
| 6,751,626 B2 | 6/2004 | Brown et al. | |
| 6,761,692 B2 | 7/2004 | Angelsen et al. | |
| 6,798,378 B1 | 9/2004 | Walters | |
| 6,816,782 B1 | 11/2004 | Walters et al. | |
| 7,002,579 B2 | 2/2006 | Olson | |
| 7,236,426 B2 | 6/2007 | Turner et al. | |
| 7,243,457 B1 | 7/2007 | Smith et al. | |
| 7,321,824 B1 | 1/2008 | Nesbitt | |
| 7,430,461 B1 | 9/2008 | Michaels | |
| 7,652,952 B2 | 1/2010 | Betts et al. | |
| 7,710,825 B2 | 5/2010 | Betts et al. | |
| 7,722,218 B2 | 5/2010 | Leung | |
| 7,729,203 B2 | 6/2010 | Betts et al. | |
| 7,755,974 B2 | 7/2010 | Betts et al. | |
| 7,812,667 B2 | 10/2010 | Fagg | |
| 7,870,496 B1 | 1/2011 | Sherwani | |
| 7,890,867 B1 | 2/2011 | Margulis | |
| 8,019,532 B2 | 9/2011 | Sheha et al. | |
| 8,040,758 B1 | 10/2011 | Dickinson | |
| 8,063,540 B2 | 11/2011 | Angelsen et al. | |
| 2001/0054961 A1 | 12/2001 | Twining | |
| 2002/0035574 A1 | 3/2002 | Dumas | |
| 2002/0093541 A1 | 7/2002 | Schileru-Key | |
| 2002/0099457 A1* | 7/2002 | Fredlund | A63B 24/0021 700/91 |
| 2003/0056419 A1 | 3/2003 | Squires et al. | |
| 2003/0089020 A1 | 5/2003 | Dirito | |
| 2004/0124297 A1 | 7/2004 | Steer | |
| 2004/0193364 A1 | 9/2004 | Chojnacki | |
| 2004/0249860 A1 | 12/2004 | Stechschulte et al. | |
| 2005/0037872 A1 | 2/2005 | Fredlund et al. | |
| 2005/0102101 A1 | 5/2005 | Beesley et al. | |
| 2006/0013066 A1 | 1/2006 | Nishimori et al. | |
| 2006/0048434 A1 | 3/2006 | Congel | |
| 2006/0119585 A1 | 6/2006 | Skinner | |
| 2006/0224940 A1 | 10/2006 | Lee | |
| 2006/0265931 A1 | 11/2006 | McFadden et al. | |
| 2007/0011334 A1 | 1/2007 | Higgins et al. | |
| 2007/0045010 A1 | 3/2007 | Kasperek | |
| 2007/0058489 A1 | 3/2007 | Bratcher | |
| 2007/0220798 A1 | 9/2007 | Davidson | |
| 2008/0126935 A1 | 5/2008 | Blomgren | |
| 2008/0165022 A1 | 7/2008 | Herz et al. | |
| 2008/0204424 A1 | 8/2008 | Jin et al. | |
| 2008/0246627 A1 | 10/2008 | Guazzelli | |
| 2009/0064055 A1 | 3/2009 | Chaudhri et al. | |
| 2009/0099871 A1 | 4/2009 | Gadodia | |
| 2009/0105952 A1 | 4/2009 | Grace et al. | |
| 2009/0179789 A1 | 7/2009 | Haughay, Jr. et al. | |
| 2009/0240354 A1 | 9/2009 | Davidson | |
| 2009/0249247 A1 | 10/2009 | Tseng et al. | |
| 2009/0258710 A1 | 10/2009 | Quatrochi | |
| 2009/0271054 A1 | 10/2009 | Dokken | |
| 2009/0287409 A1 | 11/2009 | Summers | |
| 2009/0295626 A1 | 12/2009 | Su | |
| 2010/0049468 A1 | 2/2010 | Papadourakis | |
| 2010/0080082 A1 | 4/2010 | Betts et al. | |
| 2010/0145601 A1 | 6/2010 | Kurtti et al. | |
| 2010/0199225 A1 | 8/2010 | Coleman et al. | |
| 2010/0226203 A1 | 9/2010 | Buttle et al. | |
| 2010/0250122 A1 | 9/2010 | Kubota et al. | |
| 2011/0013484 A1 | 1/2011 | Coleman et al. | |
| 2011/0013485 A1 | 1/2011 | Maguire | |
| 2011/0019887 A1 | 1/2011 | Roehrig et al. | |
| 2011/0025720 A1 | 2/2011 | Jo et al. | |
| 2011/0082644 A1 | 4/2011 | Imasaka et al. | |
| 2011/0154183 A1 | 6/2011 | Burns et al. | |
| 2011/0208479 A1 | 8/2011 | Chaves | |
| 2011/0213515 A1 | 9/2011 | Haymart et al. | |
| 2011/0214500 A1 | 9/2011 | Cabrera et al. | |
| 2011/0257819 A1 | 10/2011 | Chen et al. | |
| 2012/0001773 A1 | 1/2012 | Lyons et al. | |
| 2012/0011437 A1 | 1/2012 | James et al. | |
| 2012/0014220 A1 | 1/2012 | DePasqua | |
| 2012/0047790 A1 | 3/2012 | Hess et al. | |
| 2012/0069712 A1 | 3/2012 | Potanin et al. | |
| 2012/0106300 A1 | 5/2012 | Maguire | |
| 2012/0144384 A1 | 6/2012 | Baek | |
| 2012/0144723 A1 | 6/2012 | Davidson | |
| 2012/0185801 A1 | 7/2012 | Madonna et al. | |
| 2012/0316456 A1 | 12/2012 | Rahman et al. | |
| 2012/0317167 A1 | 12/2012 | Rahman et al. | |
| 2013/0007665 A1 | 1/2013 | Chaudhri et al. | |
| 2013/0040714 A1 | 2/2013 | Rosing | |
| 2013/0074051 A1 | 3/2013 | Freeman | |
| 2013/0096575 A1 | 4/2013 | Olson | |
| 2013/0107031 A1 | 5/2013 | Atkinson | |
| 2013/0307720 A1 | 11/2013 | Lilburn | |
| 2013/0343151 A1 | 12/2013 | Shiraki et al. | |
| 2014/0012587 A1 | 1/2014 | Park | |
| 2014/0032468 A1 | 1/2014 | Anandaraj | |
| 2014/0071059 A1 | 3/2014 | Girault | |
| 2014/0111368 A1 | 4/2014 | Lee et al. | |
| 2014/0180566 A1 | 6/2014 | Malhotra | |
| 2014/0195297 A1 | 7/2014 | Abuelsaad et al. | |
| 2014/0358483 A1 | 12/2014 | da Rosa | |

(56) References Cited

U.S. PATENT DOCUMENTS

| | | |
|---|---|---|
| 2015/0019135 A1 | 1/2015 | Kacyvenski |
| 2015/0051786 A1 | 2/2015 | Wang |
| 2015/0054655 A1 | 2/2015 | Bailey |
| 2015/0054732 A1 | 2/2015 | Bailey |
| 2015/0054828 A1 | 2/2015 | Bailey |
| 2015/0054829 A1 | 2/2015 | Bailey |
| 2015/0055827 A1 | 2/2015 | Bailey |
| 2015/0055930 A1 | 2/2015 | Bailey |
| 2015/0057929 A1 | 2/2015 | Bailey |
| 2015/0057965 A1 | 2/2015 | Gaynor |
| 2015/0057968 A1 | 2/2015 | Bailey |
| 2015/0058020 A1 | 2/2015 | Bailey |
| 2015/0058237 A1 | 2/2015 | Bailey |
| 2015/0058323 A1 | 2/2015 | Bailey |
| 2015/0310524 A1 | 10/2015 | Gospodarek et al. |
| 2016/0125348 A1 | 5/2016 | Dyer et al. |

FOREIGN PATENT DOCUMENTS

| | | |
|---|---|---|
| EP | 2 613 223 A1 | 7/2013 |
| JP | 2004 207812 A | 7/2004 |
| JP | 2006-158239 A | 6/2006 |
| JP | 2010 193284 A | 9/2010 |
| JP | 2011 139647 A | 7/2011 |
| WO | 98/02037 A1 | 1/1998 |
| WO | 2004/088572 | 10/2004 |
| WO | 2010/056392 | 5/2010 |
| WO | 2012/170163 | 12/2012 |
| WO | 2014088508 A1 | 6/2014 |
| ZA | 2003-08052 A | 7/2004 |

OTHER PUBLICATIONS

PCT International Search Report and Written Opinion; PCT/IB2014/063979; Jan. 7, 2015.
PCT International Search Report and Written Opinion; PCT/IB2014/063980; Jan. 5, 2015.
PCT International Search Report and Written Opinion; PCT/IB2014/063982; Dec. 22, 2014.
PCT International Search Report and Written Opinion; PCT/IB2014/063975; Dec. 3, 2014.
PCT International Search Report and Written Opinion; PCT/IB2014/063974; Dec. 2, 2014.
PCT International Search Report and Written Opinion; PCT/IB2013/060285; Feb. 18, 2014.
PCT International Search Report and Written Opinion; PCT/US2013/047869; Oct. 21, 2013.
PCT International Search Report and Written Opinion; PCT/US2013/048177; Oct. 21, 2013.
PCT International Search Report and Written Opinion; PCT/US2013/048129; Oct. 17, 2013.
PCT International Search Report and Written Opinion; PCT/US2013/047926; Oct. 11, 2013.
PCT International Search Report and Written Opinion; PCT/US2013/047645; Sep. 27, 2013.
Allen, et al.; Upper Extremity Kinematic Trends of Fly-Casting; Establishing the Effects of Line Length; Sports Biomechanics; vol. 7, No. 1; Jan. 1, 2008; pp. 38-53.
First look at new Mio Link ANT +/Bluetooth Smart optical heart rate wrist band; http://www.dcrainmaker.com/2014/01/mio-link-first-look.html; Jan. 6, 2014 (accessed Apr. 18, 2016).
SAS, "SAS BI Dashboard 4.31 User's Guide", Second Edition, by SAS Electronic book, Aug. 1, 2012, downloaded at http://support.sas.com/documentation/cdl/en/bidbrdug/65580/PDF/default/bidrdrug.pdf.
PCT International Search Report and Written Opinion; PCT/IB2014/063976, dated Dec. 12, 2014.
PCT International Search Report and Written Opinion; PCT/IB2014/063983, dated Mar. 5, 2015.
PCT International Search Report and Written Opinion; PCT/IB2014/063973, dated Nov. 28, 2014.
PCT International Search Report and Written Opinion; PCT/IB2014/063981, dated Feb. 10, 2015.
PCT International Search Report and Written Opinion; PCT/IB2014/063978, dated Dec. 19, 2014.
PCT International Search Report and Written Opinion; PCT/IB2014/063977, dated Nov. 28, 2014.

* cited by examiner

FISHING STATISTICS DISPLAY

CROSS-REFERENCE TO RELATED APPLICATIONS

This application claims the benefit of U.S. Provisional Patent Application Ser. No. 61/868,444, filed Aug. 21, 2013 titled FISHING DATA COLLECTION AND USE, and the disclosure of which is incorporated herein by reference.

BACKGROUND

Discussion of the Related Art

This section is intended to provide background information to facilitate a better understanding of various technologies described herein. As the section's title implies, this is a discussion of related art. That such art is related in no way implies that it is prior art. The related art may or may not be prior art. It should therefore be understood that the statements in this section are to be read in this light, and not as admissions of prior art.

Recreational and competitive fishing as a sport is growing in popularity. Fishermen engaged in these activities try to maximize their effectiveness using a variety of fishing techniques and equipment. The success of a fisherman depends in part on the ability to recognize and react to different situations and conditions. Conditions that affect fishing include weather, tide, lunar cycle, water temperature, and time, among others. In order to maximize the number of caught fish, a fisherman must understand the effect that changing conditions can have on fishing and react appropriately.

SUMMARY

Described herein are implementations of various technologies for a method for displaying fishing statistics. The method may include displaying a path. The path may be recorded by a positioning system. The path may be traveled by a fisherman or a marine vessel. The method may display one or more fishing statistics along the path.

Described herein are also implementations of various technologies for a non-transitory computer-readable medium having stored thereon computer-executable instructions which, when executed by a computer, cause the computer to perform various actions. The actions may include receiving coordinates recorded by a positioning system. The positioning system may be on a marine vessel or located near a fisherman. The actions may include receiving one or more fishing statistics. The actions may include displaying a path using the received coordinates and the fishing statistics along the path.

Described herein are also implementations of various technologies for an apparatus for displaying marine electronic navigation data. The apparatus includes one or more processors, a screen that may display marine data, a positioning system, and memory. The memory has a plurality of executable instructions. When the executable instructions are executed by the one or more processors, the one or more processors may receive coordinates. The coordinates may be recorded by the positioning system. The one or more processors may receive one or more fishing statistics. The one or more processor may display a path using the received coordinates. The one or more processors may display the fishing statistics along the path.

The above referenced summary section is provided to introduce a selection of concepts in a simplified form that are further described below in the detailed description section. The summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

Implementations of various technologies will hereafter be described with reference to the accompanying drawings. It should be understood, however, that the accompanying drawings illustrate only the various implementations described herein and are not meant to limit the scope of various technologies described herein.

DETAILED DESCRIPTION

The discussion below is directed to certain specific implementations. It is to be understood that the discussion below is only for the purpose of enabling a person with ordinary skill in the art to make and use any subject matter defined now or later by the patent "claims" found in any issued patent herein.

It is specifically intended that the claimed invention not be limited to the implementations and illustrations contained herein, but include modified forms of those implementations including portions of the implementations and combinations of elements of different implementations as come within the scope of the following claims. It should be appreciated that in the development of any such actual implementation, as in any engineering or design project, numerous implementation-specific decisions must be made to achieve the developers' specific goals, such as compliance with system-related and business related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure. Nothing in this application is considered critical or essential to the claimed invention unless explicitly indicated as being "critical" or "essential."

Reference will now be made in detail to various implementations, examples of which are illustrated in the accompanying drawings and figures. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits and networks have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first object or step could be termed a second object or step, and, similarly, a second object or step could be termed a first object or step, without departing from the scope of the invention. The first object or step, and the second object or step, are both objects or steps, respectively, but they are not to be considered the same object or step.

The terminology used in the description of the present disclosure herein is for the purpose of describing particular implementations only and is not intended to be limiting of the present disclosure. As used in the description of the present disclosure and the appended claims, the singular forms "a," "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises" and/or "comprising," when used in this specification, specify the presence of stated features, integers, steps, operations, elements, and/or components, but do not preclude the presence or addition of one or more other features, integers, steps, operations, elements, components and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context. As used herein, the terms "up" and "down"; "upper" and "lower"; "upwardly" and "downwardly"; "below" and "above"; and other similar terms indicating relative positions above or below a given point or element may be used in connection with some implementations of various technologies described herein.

Various implementations of a fishing statistics display described herein will now be described in more detail with reference to FIGS. 1-6.

Visualizing recorded fishing data, including, for example, the rate at which fishing casts were made, or the locations at which fish were caught, can be very useful for a fisherman. By reviewing the location and the number of successful and unsuccessful casts and combining this with time, season, weather, and boating condition data a fisherman can track fishing performance over time and analyze performance in certain conditions. Using this information, a fisherman may be tactically more aware for various conditions and able to implement more effective fishing plans.

Figure 1:
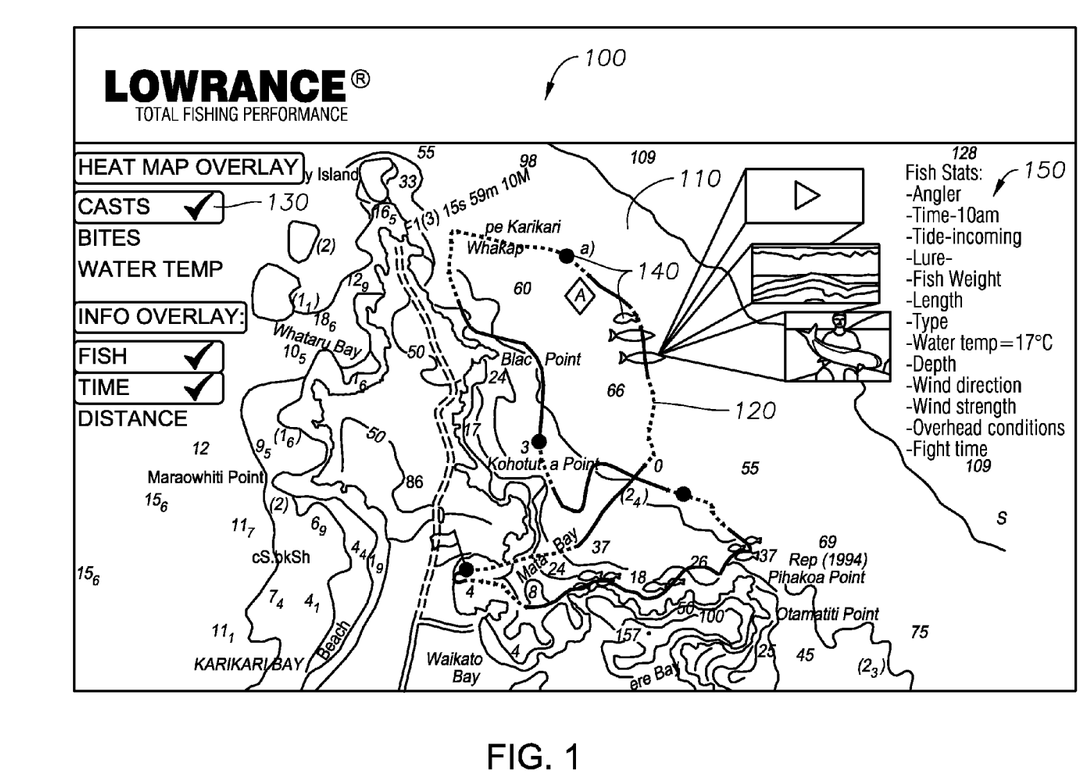
FIG. 1 illustrates a fishing statistics display in accordance with various implementations described herein.

FIG. 1 illustrates a fishing statistics display in accordance with implementations of various techniques described herein. The fishing statistics display 100 may be displayed on a marine electronics device as described in FIG. 5, a computer as described in FIG. 6, a smartphone device, or any other display device.

In the illustrated display 100, a map 110 is shown with a path 120 and fishing statistics 130 displayed along the path 120. The path 120 may have been recorded by a positioning system on a marine vessel, or by a smartphone or other device used by a fisherman. The path 120 may be drawn using a series of coordinates recorded by a positioning system. The path 120 may be filled to represent fishing statistics with patterns, colors, or any other method to display fishing statistics on the path 120. In FIG. 1, path 120 is displayed as a dotted line to indicate areas where the rate at which casts occurred was greater than average, and as a solid line to indicate areas where the rate at which casts occurred was less than average. In another implementation, the path 120 may be colored green in areas where the cast rate was the greatest, red in areas where the cast rate was the lowest, and yellow in areas in where the cast rate was between the greatest and lowest.

The fishing statistics 130 displayed along the path 120 may be a ratio of a number of casts to a number of caught fish, a ratio of a number of casts to a number of bites, a ratio of a number of caught fish to a number of bites, a rate at which casts are made over time, a rate at which bites occur over time, and a rate at which catches occur over time, or any other statistic related to fishing. The fishing statistics 130 may be recorded statistics, or predictions created through the use of recorded data. The path 120 may contain icons 140 to indicate the location of a recorded event or recorded piece of information. For instance, these icons 140 may indicate the location of a catch, a bite, a saved location, or any other event that may occur on a fishing trip. The illustrated icons 140 in FIG. 1 are either black dots or drawings of fish, but any symbol may be used as an icon 140.

The display 100 may include additional information 150 located near the path 120. The additional information 150 may relate to a location on the path 120, or may relate to a caught fish. The additional information 150 may contain information recorded when the marine vessel or fisherman was at the location on the path 120, information recorded when a fish was caught, and information describing conditions at the time the marine vessel or fisherman was at the location on the path 120. The additional information 150 may include the identity of the fisherman, time, tidal data, information regarding the equipment used, information about a caught fish including length, weight, fight time, and type, water temperature, weather information including wind direction, strength, and overhead conditions, the moon phase, the time of sunrise and sunset, or any other relevant information. For example, if a location on a path 120 is selected, and no fish was caught at the selected location, the additional information 150 may include the identity of the fisherman, the time, the tidal data, water temperature, weather information, moon phase, and time of sunrise and sunset. If the same location were selected but a fish had been caught at the location, then the additional information 150 may also include the equipment used, length, weight, fight time, and type of fish caught, captured sonar information, and images or video of the fish being caught.

The additional information 150 may be recorded using sensors on a vessel or may be determined through other sources. For example, weather information may be determined using a database accessible through the Internet. This data collection process and fishing statistic storage is described in further detail in FIG. 3.

In one implementation, a user may select a location at or near a location on the path 120 or an icon 140 and additional information 150 regarding the selection will be displayed. The additional information 150 may be displayed as images or videos corresponding to the selected location, or sonar information recorded at the selected location, and may include pictures of a caught fish or video of a fish being caught. The additional information 150 may be visually linked to the relevant location. For example, the additional information 150 may be drawn to look as if it is rising from the relevant location, as shown in FIG. 1. In another example, the additional information 150 may be displayed in a window overlaid on the display 100.

Figure 2:
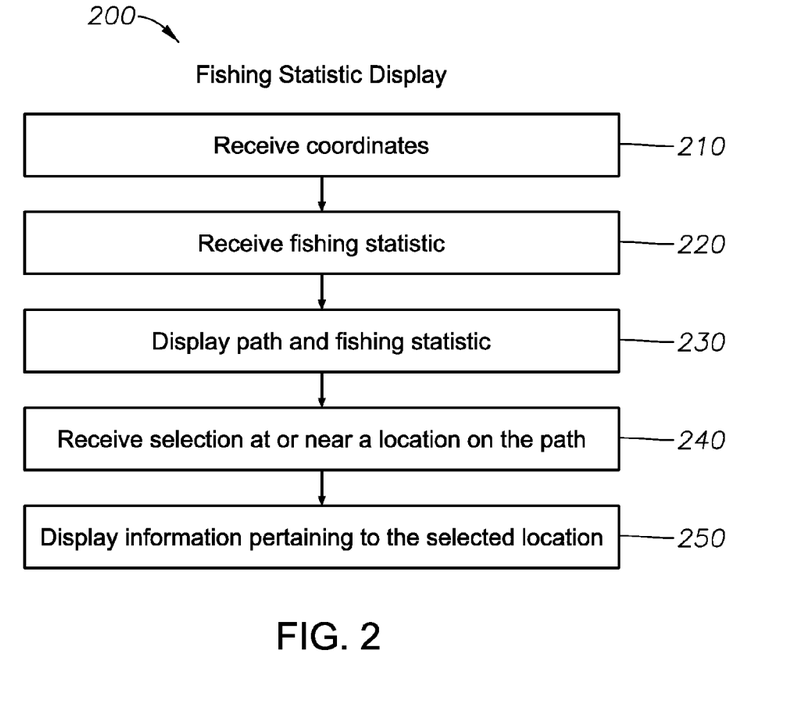
FIG. 2 illustrates a flow diagram of a method for displaying fishing statistics in accordance with various implementations described herein.

FIG. 2 illustrates a flow diagram of a method 200 for displaying fishing statistics in accordance with implementations of various techniques described herein. In one implementation, method 200 may be performed by any computing device, such as computer 600, described below, a marine electronics device 500, described below, or a smart phone. It should be understood that while method 200 indicates a particular order of execution of operations, in some implementations, certain portions of the operations may be executed in a different order. Further, in some implementations, additional operations or steps may be added to method 200. Likewise, some operations or steps may be omitted. Additionally, the operations may be executed on more than one computer 600 or other device.

As mentioned above, the computer 600 may be loaded with a set of instructions (software) to perform method 200. At block 210, the software may receive a set of coordinates recorded on a marine vessel or by a device located near a fisherman. The received coordinates may be determined using a positioning system. The positioning system may be a satellite positioning system, such as a Global Positioning System (GPS), or a radio beacon positioning system, such as Loran™. The received coordinates may be latitude and longitude coordinates. The coordinates may be received with the time at which the position was recorded.

At block 220, the software may receive one or more fishing statistics. The fishing statistics may be a ratio of casts to caught fish, a ratio of casts to bites, a rate at which casts are made over time, a rate at which bites occur over time, and a rate at which catches occur over time, or any other statistics related to fishing. The fishing statistics may include location data paired with the statistics. For example, the fishing statistics may be the rate at which casts are made during each 50 meters traveled during a fishing trip, or the fishing statistics may be the ratio of casts to caught fish for each 50 meters traveled during a fishing trip. In another example, the fishing statistics may be the rate at which casts occurred during each 10 minute period of a fishing trip, or the rate at which catches occurred during each 10 minute period of a fishing trip.

At block 230, the software may display a path 120 using the received set of coordinates, and the software may display the fishing statistics along the path 120. In one implementation, the fishing statistics may be displayed as colors or patterns at locations on the path 120. For example, for every segment of the path 120 in which the cast to bite ratio is greater than 1, the path 120 may be colored green, and any other segment may be colored red. Alternately, the path 120 may be colored green in areas where the cast to catch ratio is above the average for the trip, and red in areas where the cast to catch ratio is below the average for the trip. In another example, the path 120 may be colored green in areas where the rate at which casts were made over time is highest, red in areas where the rate at which casts were made over time is lowest, and various blends of the two colors, such as orange, in areas where the rate at which casts were made over time is between the highest and lowest. In another implementation, the path 120 may contain a pattern to represent the fishing statistics. In yet another implementation, the path 120 may contain icons 140 to represent the fishing statistics. In still another implementation, the software may display multiple fishing statistics or multiple ratios along the path 120.

At block 240, the software may receive a selection at or near a location on the displayed path 120. The selection may be a location on the path 120, or an icon 140.

At block 250, the software may display additional information 150 pertaining to the selected location. The additional information 150 may contain information recorded when the marine vessel or fisherman was at the location on the path, or information describing conditions at the time the marine vessel was at the location on the path. The additional information 150 may include the identity of the fisherman, time, tidal data, information regarding the equipment used, information about a caught fish including length, weight, fight time, and type, water temperature, weather information including wind direction, strength, and overhead conditions, the moon phase, the time of sunrise and sunset, or any other relevant information. The additional information 150 may be displayed as images or videos corresponding to the selected location, or sonar information recorded at the selected location, and may include pictures of a caught fish or video of a fish being caught.

Figure 3:
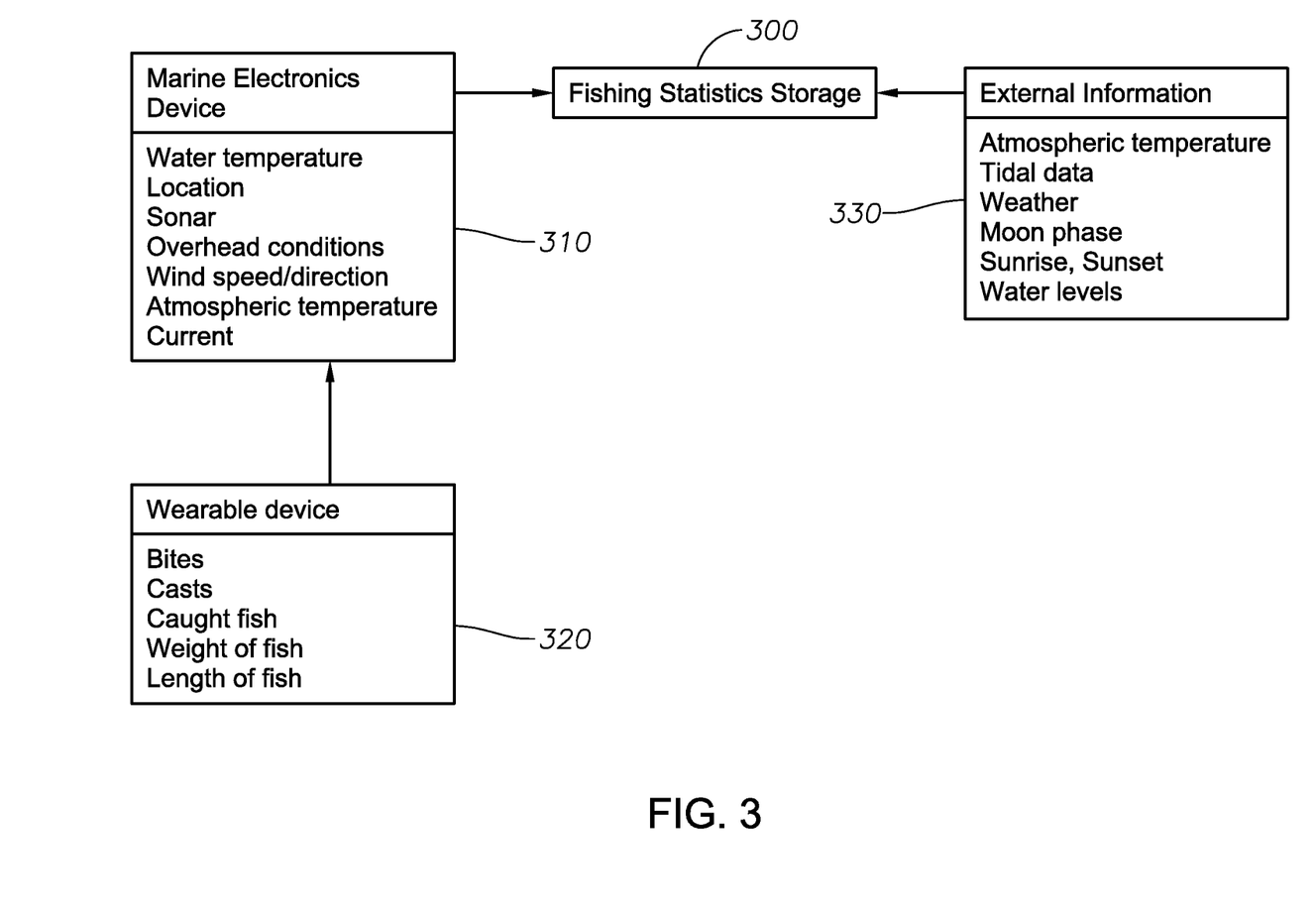
FIG. 3 illustrates a diagram of data sources used to collect fishing statistics in accordance with various implementations described herein.

FIG. 3 illustrates a diagram of data sources used to collect fishing statistics in accordance with implementations of various techniques described herein. The collected fishing statistics may be accessed in fishing statistics storage 300 and displayed on a fishing statistics display 100. Data from various sources may be transferred to fishing statistics storage 300. Fishing statistics storage 300 may be located on a computer system 600. In one implementation, fishing statistics storage 300 may be implemented as a cloud service. Fishing statistics storage 300 may be implemented on any device capable of collecting and storing fishing statistics.

Figure 4:
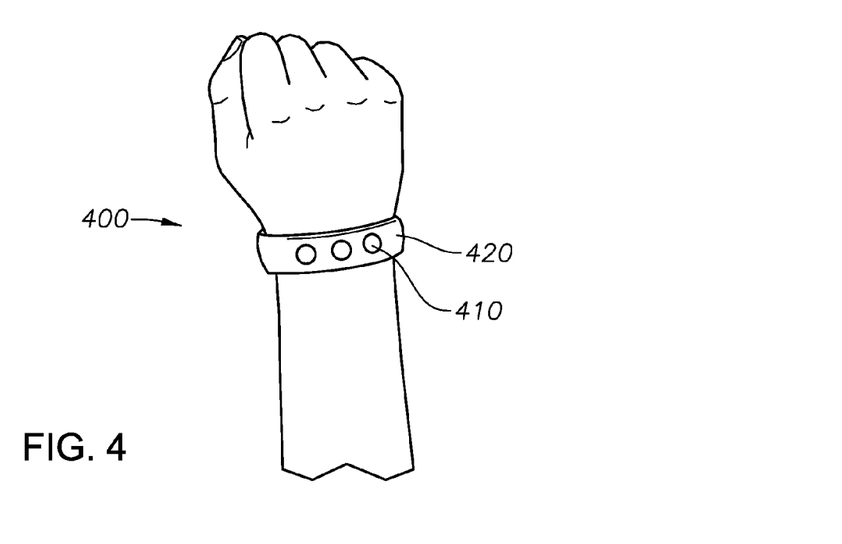
FIG. 4 illustrates a wearable electronic device used to collect fishing statistics in accordance with various implementations described herein.

Wearable electronic device 320, described in further detail in FIG. 4, may collect fishing statistics such as bites, casts, caught fish, the weight of a caught fish, the length of a caught fish, and other fishing statistics. The fishing statistics collected using wearable electronic device 320 may be transmitted to a marine electronics device 310, or directly to fishing statistics storage 300. The marine electronics device 310 is described in more detail with reference to FIG. 5.

The marine electronics device 310 may collect fishing statistics such as water temperature, location, sonar, overhead conditions, wind speed and direction, atmospheric temperature, current, and other fishing statistics. This information may be transmitted directly to fishing statistics storage 300, or may be transmitted to another device, such as a smart phone, and then transmitted to fishing statistics storage 300.

External information 330 may also be retrieved and stored in fishing statistics storage 300. The external information 330 may be retrieved from the Internet or any other source by a computer system 600. Further, the external information 330 may be transmitted to fishing statistics storage 300 in the form of a database or any other format. The external information 330 may include atmospheric temperature, tidal data, weather, moon phase, sunrise, sunset, water levels, or any other fishing statistics.

Wearable Electronic Device

FIG. 4 illustrates a wearable electronic device 400 used to collect fishing statistics in accordance with various implementations described herein. The wearable electronic device 400 may be worn around a fisherman's arm or wrist. The wearable electronic device 400 may also be attached to a fishing rod. The wearable electronic device 400 may include a housing 420. The housing 420 may be in the shape of a band. The housing 420 may be made of a combination of plastics and rubbers, or of any other synthetic material.

The wearable electronic device 400 may include one or more buttons 410. The one or more buttons 410 may be used for user input, such as to indicate the occurrence of a bite or catch, or to input the length and weight of a caught fish. The wearable electronic device 400 may contain a computer 600 and motion sensors or other sensors. Using the sensors, wearable electronic device 400 may capture fishing statistics during a fishing trip. Wearable electronic device 400 may count casts, determine the type of cast used, determine the occurrence of a bite or catch, determine the weight and length of a caught fish, the number of caught fish, or other fishing statistics. The fishing statistics may be recorded in memory. The wearable electronic device 400 may contain wireless technology, such as Bluetooth™ or Wi-Fi™. The wearable electronic device 400 may use the wireless technology to transmit recorded statistics to a marine electronics device 500, a smart phone, or any other computer system 600 or fishing statistic storage device 300.

Marine Electronics Device

Figure 5:
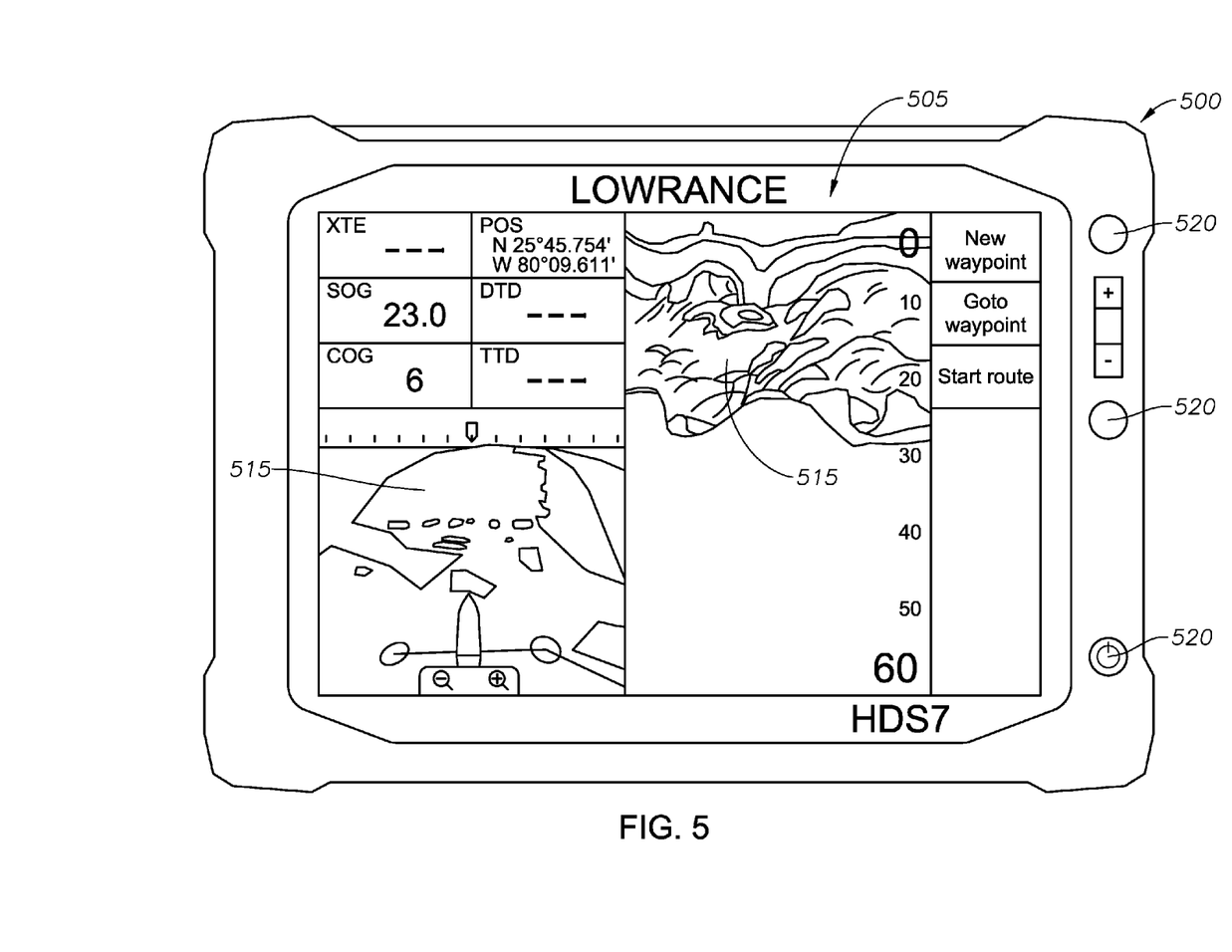
FIG. 5 illustrates a schematic of a marine electronics device in accordance with implementations of various techniques described herein.

FIG. 5 illustrates a schematic diagram of a marine electronics device 500 in accordance with various implementations described herein. The marine electronics device 500 includes a screen 505. In certain implementations, the screen 505 may be sensitive to touching by a finger. In other implementations, the screen 505 may be sensitive to the body heat from the finger, a stylus, or responsive to a mouse. The marine electronics device 500 may display marine electronic data 515. The marine electronic data types 515 may include chart data, radar data, sonar data, steering data, dashboard data, navigation data, a fishing statistics display 100, and the like. The marine electronics device 500 may also include a plurality of buttons 520, which may be either physical buttons or virtual buttons, or a combination thereof. The marine electronics device may include a computer system 600, which is described in more detail with reference to FIG. 6.

A fishing statistics display 100 may be displayed and updated on a marine electronics device 500 in real time during a fishing trip. The marine electronics device 500 may contain a positioning system or receive positioning system coordinates from an attached device. The marine electronics device 500 may also receive fishing statistics from sensors contained within or attached to the marine electronics device 500, or from another device transmitting fishing statistics to the marine electronics device, such as a wearable electronic device 400. The marine electronics device 500 may process the positioning system coordinates and the collected or received fishing statistics throughout a fishing trip, and then update the fishing statistic display 100 to include information captured during the fishing trip. The fishing statistic display 100 may be updated constantly throughout a fishing trip or at specified intervals during the trip.

Computing System

Implementations of various technologies described herein may be operational with numerous general purpose or special purpose computing system environments or configurations. Examples of well known computing systems, environments, and/or configurations that may be suitable for use with the various technologies described herein include, but are not limited to, personal computers, server computers, hand-held or laptop devices, multiprocessor systems, microprocessor-based systems, set top boxes, programmable consumer electronics, network PCs, minicomputers, mainframe computers, smart phones, and the like.

The various technologies described herein may be implemented in the general context of computer-executable instructions, such as program modules, being executed by a computer. Generally, program modules include routines, programs, objects, components, data structures, etc. that performs particular tasks or implement particular abstract data types. Further, each program module may be implemented in its own way, and all need not be implemented the same way. While program modules may all execute on a single computing system, it should be appreciated that, in some implementations, program modules may be implemented on separate computing systems or devices adapted to communicate with one another. A program module may also be some combination of hardware and software where particular tasks performed by the program module may be done either through hardware, software, or both.

The various technologies described herein may also be implemented in distributed computing environments where tasks are performed by remote processing devices that are linked through a communications network, e.g., by hard-wired links, wireless links, or combinations thereof. In a distributed computing environment, program modules may be located in both local and remote computer storage media including memory storage devices.

Figure 6:
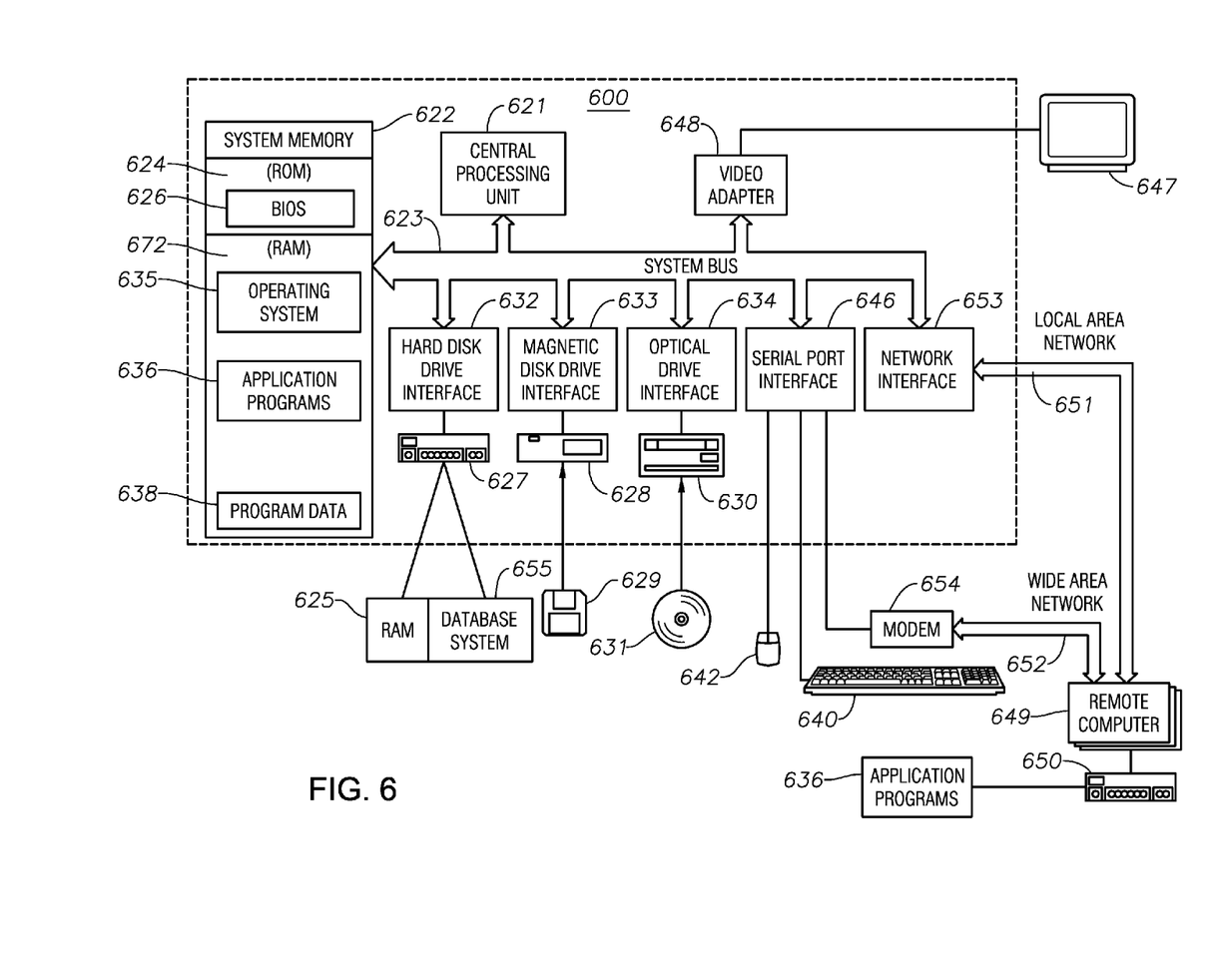
FIG. 6 illustrates a schematic diagram of a computing system in which the various technologies described herein may be incorporated and practiced.

FIG. 6 illustrates a computer system 600 into which implementations of various technologies and techniques described herein may be implemented. Computing system 600 may be a conventional desktop, a handheld device, a wearable electronic device, a controller, a personal digital assistant, a server computer, an electronic device/instrument, a laptop, a tablet, or part of a navigation system, marine electronics, or sonar system. It should be noted, however, that other computer system configurations may be used.

The computing system 600 may include a central processing unit (CPU) 621, a system memory 622 and a system bus 623 that couples various system components including the system memory 622 to the CPU 621. Although only one CPU is illustrated in FIG. 6, it should be understood that in some implementations the computing system 600 may include more than one CPU. The system bus 623 may be any of several types of bus structures, including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus. The system memory 622 may include a read only memory (ROM) 624 and a random access memory (RAM) 625. A basic input/output system (BIOS) 626, containing the basic routines that help transfer information between elements within the computing system 600, such as during start-up, may be stored in the ROM 624. The computing system may be implemented using a printed circuit board containing various components including processing units, data storage memory, and connectors.

The computing system 600 may further include a hard disk drive 627 for reading from and writing to a hard disk, a magnetic disk drive 628 for reading from and writing to a removable magnetic disk 629, and an optical disk drive 630 for reading from and writing to a removable optical disk 631, such as a CD ROM or other optical media. The hard disk drive 627, the magnetic disk drive 628, and the optical disk drive 630 may be connected to the system bus 623 by a hard disk drive interface 632, a magnetic disk drive interface 633, and an optical drive interface 634, respectively. The drives and their associated computer-readable media may provide nonvolatile storage of computer-readable instructions, data structures, program modules and other data for the computing system 600.

Although the computing system 600 is described herein as having a hard disk, a removable magnetic disk 629 and a removable optical disk 631, it should be appreciated by those skilled in the art that the computing system 600 may also include other types of computer-readable media that may be accessed by a computer. For example, such computer-readable media may include computer storage media and communication media. Computer storage media may include volatile and non-volatile, and removable and non-removable media implemented in any method or technology for storage of information, such as computer-readable instructions, data structures, program modules or other data. Computer storage media may further include RAM, ROM, erasable programmable read-only memory (EPROM), electrically erasable programmable read-only memory (EEPROM), flash memory or other solid state memory technology, CD-ROM, digital versatile disks (DVD), or other optical storage, magnetic cassettes, magnetic tape, magnetic disk storage or other magnetic storage devices, or any other medium which can be used to store the desired information and which can be accessed by the computing system 600. Communication media may embody computer readable instructions, data structures, program modules or other data in a modulated data signal, such as a carrier wave or other transport mechanism and may include any information delivery media. By way of example, and not limitation, communication media may include wired media such as a wired network or direct-wired connection, and wireless media such as acoustic, RF, infrared and other wireless media. Combinations of any of the above may also be included within the scope of computer readable media.

A number of program modules may be stored on the hard disk 627, magnetic disk 629, optical disk 631, ROM 624 or RAM 625, including an operating system 635, one or more application programs 636, program data 638, and a database system 655. The one or more application programs 636 may contain program instructions configured to perform method 200 according to various implementations described herein. The operating system 635 may be any suitable operating system that may control the operation of a networked personal or server computer, such as Windows® XP, Mac OS® X, Unix-variants (e.g., Linux® and BSD®), and the like.

A user may enter commands and information into the computing system 600 through input devices such as a keyboard 640 and pointing device 642. Other input devices may include a microphone, joystick, game pad, satellite dish, scanner, user input button, or the like. These and other input devices may be connected to the CPU 621 through a serial port interface 646 coupled to system bus 623, but may be connected by other interfaces, such as a parallel port, game port or a universal serial bus (USB). A monitor 647 or other type of display device may also be connected to system bus 623 via an interface, such as a video adapter 648. In addition to the monitor 647, the computing system 600 may further include other peripheral output devices such as speakers and printers.

Further, the computing system 600 may operate in a networked environment using logical connections to one or more remote computers 649. The logical connections may be any connection that is commonplace in offices, enterprise-wide computer networks, intranets, and the Internet, such as local area network (LAN) 651 and a wide area network (WAN) 652. The remote computers 649 may each include application programs 636 similar to that as described above. The computing system 600 may use a Bluetooth radio to wirelessly communicate with another device.

When using a LAN networking environment, the computing system 600 may be connected to the local network 651 through a network interface or adapter 653. When used in a WAN networking environment, the computing system 600 may include a modem 654, wireless router or other means for establishing communication over a wide area network 652, such as the Internet. The modem 654, which may be internal or external, may be connected to the system bus 623 via the serial port interface 646. In a networked environment, program modules depicted relative to the computing system 600, or portions thereof, may be stored in a remote memory storage device 650. It will be appreciated that the network connections shown are exemplary and other means of establishing a communications link between the computers may be used.

While the foregoing is directed to implementations of various techniques described herein, other and further implementations may be devised without departing from the basic scope thereof, which may be determined by the claims that follow. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method for displaying fishing statistics on a marine electronics device, the method comprising:
   receiving at the marine electronics device, from a wearable device used by a fisherman, fishing data corresponding to one or more fishing statistics that occurred during a fishing trip in a marine vessel on a body of water, wherein the one or more fishing statistics comprise at least one of cast information, bite information, catch information, or associated rate information, wherein the wearable device is configured to detect the fishing data using at least one of one or more motion sensors or one or more buttons, and wherein the wearable device is not connected to a fishing line;
   determining one or more locations traveled by the marine vessel associated with the fishing data such that each fishing statistic is associated with at least one location; and
   displaying, on a screen of the marine electronics device, a path traveled by the marine vessel during the fishing trip on the body of water, wherein the path is displayed such that one or more portions of the path are altered to form a heat map to indicate the occurrence of the one or more fishing statistics at the corresponding location along the path, wherein the altered one or more portions of the path define at least one of an altered pattern or an altered color.

2. The method of claim 1, wherein the fishing statistics comprise a rate at which casts were made over time, a rate at which bites occurred over time, a rate at which catches were made over time, a ratio of a number of caught fish to a number of casts made, a ratio of a number of bites to a number of casts made, a ratio of a number of caught fish to a number of bites, or combinations thereof.

3. The method of claim 1, wherein displaying the path comprises:
- displaying a first one or more portions of the path in a first color or pattern where a rate of occurrence of one or more fishing statistics is highest;
- displaying a second one or more portions of the path in a second color or pattern where a rate of occurrence of one or more fishing statistics is lowest; and
- displaying varying combinations of the first and second color or pattern at additional one or more portions of the path where a rate of occurrence of one or more fishing statistics is between the highest and lowest rate such that the altered pattern or color for portions of the path correspond to the degree of the rate of occurrence of one or more fishing statistics along the corresponding portions of the path.

4. The method of claim 1, further comprising displaying an icon at locations along the path at which fish were caught.

5. The method of claim 1, further comprising:
- receiving a selection of a location along the path; and
- displaying, in response to receiving the selection, additional information associated with the fishing data associated with the location, wherein the additional information comprises at least one of a time of day, tidal information, a water temperature, a water depth, a wind direction, wind strength, overhead conditions, or images or videos.

6. The method of claim 5, wherein the additional information is generated from a sonar system of the marine vessel.

7. The method of claim 1, wherein the one or more fishing statistics are retrieved from fishing statistic storage.

8. A non-transitory computer-readable medium having stored thereon computer-executable instructions which, when executed by a computer, cause the computer to:
- receive, at the marine electronics device, from a wearable device used by a fisherman, fishing data corresponding to one or more fishing statistics that occurred during a fishing trip in a marine vessel on a body of water, wherein the one or more fishing statistics comprise at least one of cast information, bite information, catch information, or associated rate information, wherein the wearable device is configured to detect the fishing data using at least one of one or more motion sensors or one or more buttons, and wherein the wearable device is not connected to a fishing line;
- determine one or more locations traveled by the marine vessel associated with the fishing data such that each fishing statistic is associated with at least one location; and
- display, on a screen of the marine electronics device, a path traveled by the marine vessel during the fishing trip on the body of water, wherein the path is displayed such that one or more portions of the path are altered to form a heat map to indicate the occurrence of the one or more fishing statistics at the corresponding location along the path, wherein the altered one or more portions of the path define at least one of an altered pattern or an altered color.

9. The non-transitory computer-readable medium of claim 8, wherein the fishing statistics comprise a rate at which casts were made over time, a rate at which bites occurred over time, a rate at which catches were made over time, a ratio of a number of caught fish to a number of casts made, a ratio of a number of bites to a number of casts made, a ratio of a number of caught fish to a number of bites, or combinations thereof.

10. The non-transitory computer-readable medium of claim 8, wherein the computer-executable instructions further cause the computer to:
- receive a selection of a location on the displayed path; and
- display, in response to receiving the selection, additional information associated with the fishing data associated with the selected location, wherein the additional information comprises at least one of a time of day, tidal information, a water temperature, a water depth, a wind direction, wind strength, overhead conditions, or captured images or videos.

11. The non-transitory computer-readable medium of claim 10, wherein the additional information is generated from a sonar system of the marine vessel.

12. The non-transitory computer-readable medium of claim 8, wherein the computer-executable instructions further cause the computer to display the path by:
- displaying a first one or more portions of the path in a first color or pattern where a rate of occurrence of one or more fishing statistics is highest;
- displaying a second one or more portions of the path in a second color or pattern where a rate of occurrence of one or more fishing statistics is lowest; and
- displaying varying combinations of the first and second color or pattern at additional one or more portions of the path where a rate of occurrence of one or more fishing statistics is between the highest and lowest rate such that the altered pattern or color for portions of the path correspond to the degree of the rate of occurrence of one or more fishing statistics along the corresponding portions of the path.

13. An apparatus for displaying marine electronic data, the apparatus comprising:
- a marine electronics device having:
  - one or more processors;
  - a screen configured to display marine data; and
  - memory having a plurality of executable instructions which, when executed by the one or more processors, cause the one or more processors to:
    - receive, at the marine electronics device, from a wearable device used by a fisherman, fishing data corresponding to one or more fishing statistics that occurred during a fishing trip in a marine vessel on a body of water, wherein the one or more fishing statistics comprise at least one of cast information, bite information, catch information, or associated rate information, wherein the wearable device is configured to detect the fishing data using at least one of one or more motion sensors or one or more buttons, and wherein the wearable device is not connected to a fishing line;
    - determine one or more locations traveled by the marine vessel associated with the fishing data such that each fishing statistic is associated with at least one location; and
    - display, on the screen of the marine electronics device, a path traveled by the marine vessel during the fishing trip on the body of water, wherein the path is displayed such that one or more portions of the path are altered to form a heat map to indicate the occurrence of the fishing statistics at the corresponding location along the path, wherein the altered one or more portions of the path define at least one of an altered pattern or an altered color.

14. The apparatus of claim 13, wherein the executable instructions further cause the processor to:
receive a selection of a location along the path; and
display, in response to receiving the selection, additional information associated with the fishing data associated with the selected location, wherein the additional information comprises at least one of a time of day, tidal information, a water temperature, a water depth, a wind direction, wind strength, overhead conditions, or images or videos.

15. The apparatus of claim 14, wherein the additional information is generated from a sonar system of the marine vessel.

16. The apparatus of claim 13, wherein the fishing statistics comprise a rate at which casts were made over time, a rate at which bites occurred over time, a rate at which catches were made over time, a ratio of a number of caught fish to a number of casts made, a ratio of a number of bites to a number of casts made, a ratio of a number of caught fish to a number of bites, or combinations thereof.

17. The apparatus of claim 13, wherein the executable instructions further cause the processor to display the path by:
displaying a first one or more portions of the path in a first color or pattern where a rate of occurrence of one or more fishing statistics is highest;
displaying a second one or more portions of the path in a second color or pattern where a rate of occurrence of one or more fishing statistics is lowest; and
displaying varying combinations of the first and second color or pattern at additional one or more portions of the path where a rate of occurrence of one or more fishing statistics is between the highest and lowest rate such that the altered pattern or color for portions of the path correspond to the degree of the rate of occurrence of one or more fishing statistics along the corresponding portions of the path.

* * * * *